(12) United States Patent
Sutter et al.

(10) Patent No.: US 11,964,998 B2
(45) Date of Patent: Apr. 23, 2024

(54) METHOD FOR PURIFYING ANTI-IL-6 RECEPTOR ANTIBODIES

(71) Applicant: FRESENIUS KABI DEUTSCHLAND GMBH, Bad Homburg (DE)

(72) Inventors: Harry-James Sutter, Vevey (CH); Xavier Le Saout, Clarens (CH)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 881 days.

(21) Appl. No.: 16/635,134

(22) PCT Filed: Aug. 30, 2018

(86) PCT No.: PCT/EP2018/073345
§ 371 (c)(1),
(2) Date: Jan. 29, 2020

(87) PCT Pub. No.: WO2019/043096
PCT Pub. Date: Mar. 7, 2019

(65) Prior Publication Data
US 2020/0165295 A1 May 28, 2020

(30) Foreign Application Priority Data
Aug. 30, 2017 (EP) .................................. 17188660

(51) Int. Cl.
| | | |
|---|---|---|
| C07K 1/16 | (2006.01) |
| B01D 15/38 | (2006.01) |
| C07K 1/22 | (2006.01) |
| C07K 1/36 | (2006.01) |
| C07K 16/06 | (2006.01) |
| C07K 16/24 | (2006.01) |
| C07K 16/28 | (2006.01) |

(52) U.S. Cl.
CPC .......... C07K 1/165 (2013.01); B01D 15/3809 (2013.01); C07K 1/22 (2013.01); C07K 16/065 (2013.01); C07K 16/248 (2013.01); C07K 16/2866 (2013.01); C07K 2317/24 (2013.01)

(58) Field of Classification Search
CPC . C07K 1/16; C07K 1/36; C07K 16/28; C07K 1/22
USPC ......................................................... 530/413
See application file for complete search history.

(56) References Cited

U.S. PATENT DOCUMENTS

2021/0130396 A1 * 5/2021 Sutter ...................... C07K 1/36
2022/0194981 A1 * 6/2022 Keszey .................. B01D 15/12

FOREIGN PATENT DOCUMENTS

| JP | 2013234154 | * | 11/2013 |
| WO | WO 2008/025747 A1 | | 3/2008 |
| WO | WO 2009/092014 A1 | | 7/2009 |
| WO | WO 2009/126603 A1 | | 10/2009 |
| WO | WO 2104/161940 | * | 4/2014 |
| WO | WO 2015/070068 A1 | | 5/2015 |
| WO | WO 2017/022651 | * | 7/2016 |
| WO | WO 2017/218977 | * | 6/2017 |

OTHER PUBLICATIONS

Chen et al., (J.cHromatography 1217:216-224 (2010); online Sep. 23, 2009).*
Herzer et al., (Biotechnology and Bioengineering 112(7):1417-1428 (Jul. 2015)).*
Li (Protein Expression and Purification 134:96-103 (2017)).*
Chen et al (Journal of Chromatography A, 1217 (2010) 216-224).*

* cited by examiner

Primary Examiner — Lynn A Bristol
(74) Attorney, Agent, or Firm — James S. Keddie; Bozicevic, Field & Francis LLP

(57) ABSTRACT

The present invention relates to a method for purifying anti-IL-6 receptor antibodies from a sample comprising said antibodies and impurities, through the use of a three-chromatographic columns procedure, including a chromatography on Fluorapatite-containing resin. The invention is also concerned with pharmaceutical compositions comprising the purified antibodies obtainable by the process of the invention.

8 Claims, No Drawings

Specification includes a Sequence Listing.

METHOD FOR PURIFYING ANTI-IL-6 RECEPTOR ANTIBODIES

CROSS-REFERENCE TO RELATED APPLICATIONS

This application is a § 371 national phase of International Application No. PCT/EP2018/073345, filed on Aug. 30, 2018, which claims the benefit of European Application No. 17188660.9, filed on Aug. 30, 2017, which applications are incorporated by reference herein.

FIELD OF THE INVENTION

The present invention relates to a method for purifying anti-IL-6 receptor antibodies from a sample comprising said antibodies and impurities, through the use of a three-chromatographic columns procedure, including a chromatography on Fluorapatite-containing resin. The invention is also concerned with pharmaceutical compositions comprising the purified antibodies obtainable by the process of the invention.

BACKGROUND OF THE INVENTION

When an antibody is produced for therapeutical use, it is important to remove process related impurities, as they may be toxic. Process related impurities typically consist of HCPs (host cell proteins), DNA and rPA (residual protein A). HCPs are an important source of impurity and may represent a serious challenge due to their high complexity and heterogeneity in molecular mass, isoelectric point and structure. It is thus necessary to have therapeutic antibodies exhibiting very low levels of HCPs: a particular emphasis should be laid on the optimization of techniques to reduce HCPs during the downstream process (i.e. purification process). Furthermore the downstream process must be tailored in such a way as to comply with the quality produced by the corresponding upstream process. Product related impurities such as aggregates, antibody fragments must also be reduced to a minimal level for any kind of therapeutic antibodies.

There is a need to find optimal purification sequence which guarantees the overall clearance of product and process related impurities according to quality criteria, while minimizing protein loss due to the purification process.

SUMMARY OF THE INVENTION

In one aspect, the present invention provides a method of purifying an anti-IL-6 receptor antibody from a sample containing the antibody to be purified and impurities, wherein the method comprises the following steps: (a) contacting the sample containing the anti-IL-6 receptor antibody and the impurities with a Protein A chromatography material under conditions such that the antibody binds to the resin and at least a portion of the impurities does not bind to the resin; (b) eluting the antibody from the Protein A chromatography material, in order to obtain an eluate; (c) loading the eluate of step (b) onto a first mixed mode chromatography material under conditions such that the antibody does not bind to the resin and at least a portion of the remaining impurities binds to the resin; (d) recovering the flowthrough containing the antibody under conditions such that said recovered flowthrough contains a lower level of impurities than the eluate of step (b), (e) loading the recovered flowthrough containing the antibody of step (d) onto a second mixed mode chromatography material under conditions such that the antibody does not bind to the resin and at least a portion of the remaining impurities binds to the resin; and (f) recovering the flowthrough containing the antibody under conditions such that said recovered flowthrough contains a lower level of impurities than the recovered flowthrough of step (d).

In another aspect, the present invention also provides a method of obtaining an anti-IL-6 receptor antibody in a monomeric form, wherein the method comprises the following steps: (a) contacting the sample containing the antibody in monomeric form, aggregated form and/or fragmented form with a Protein A chromatography material under conditions such that the antibody binds to the resin and at least a portion of the aggregated form and fragmented form does not bind to the resin; (b) eluting the antibody in monomeric form from the Protein A chromatography material, in order to obtain an eluate; (c) loading the eluate of step (b) onto a first mixed mode chromatography material under conditions such that the antibody in monomeric form does not bind to the resin and at least a portion of the remaining aggregated form and fragmented form bind to the resin; (d) recovering the flowthrough containing the antibody in monomeric form under conditions such that said recovered flowthrough contains a lower level of aggregated form and fragmented form than the eluate of step (b), (e) loading the recovered flowthrough containing the antibody in monomeric form of step (d) onto a second mixed mode chromatography material under conditions such that the antibody in monomeric form does not bind to the resin and at least a portion of the remaining aggregated form and fragmented form bind to the resin; and (f) recovering the flowthrough containing the antibody in monomeric form under conditions such that said recovered flowthrough contains a lower level of aggregated form and fragmented form than the recovered flowthrough of step (d).

In one aspect, the anti-IL-6 receptor antibody to be purified according to the present invention is a monoclonal antibody, such as a monoclonal antibody selected from the group consisting of a chimeric antibody, a humanized antibody or a fully human antibody. It is preferably tocilizumab.

The mixed mode supports of the present invention present a combination of two or more of the following functionalities such as cation exchange, anion exchange, hydrophobic interaction, hydrophilic interaction, hydrogen bonding, pi-pi bonding, and metal affinity. Preferably, the mixed mode support for steps (c) is for instance selected from the group consisting of cation exchange and anion exchange, such as CAPTO™ MMC and CAPTO™ adhere, and the mixed mode support of step (e) is selected from the group consisting of hydroxyfluorapatite or fluorapatite.

The inventors have identified that methods of the invention advantageously keep product-related impurities (e.g. antibody aggregates and fragments), and process-related impurities including host cell proteins, DNA levels, and residual PA, within acceptable ranges. Methods of the invention also advantageously avoid substantial product loss and therefore allow purification of high quality antibodies at high yield.

Definition

The term "antibody", and its plural form "antibodies", includes, inter alia, polyclonal antibodies, affinity-purified polyclonal antibodies, monoclonal antibodies, and antigen-binding fragments, such as F(ab')2, Fab proteolytic fragments, and single chain variable region fragments (scFvs). Genetically engineered intact antibodies or fragments, such as chimeric antibodies, humanised antibodies, human or fully human antibodies, scFv and Fab fragments, as well as synthetic antigen-binding peptides and polypeptides, are also included.

The term "anti-IL-6 receptor antibody" or "anti-IL-6R antibody" refers to an antibody, such as a monoclonal antibody, binding to the IL-6 receptor. The "anti-IL-6 receptor antibody" is preferably a humanized monoclonal antibody; preferably tocilizumab. The light chain of tocilizumab contains an amino acid sequence as defined in SEQ ID No. 1 and the heavy chain of tocilizumab contains an amino acid sequence as defined in SEQ ID No. 2.

The term "monoclonal antibody" refers to an antibody that is a clone of a unique parent cell.

The term "humanized" immunoglobulin (or "humanized antibody") refers to an immunoglobulin comprising a human framework region and one or more CDRs from a non-human (usually a mouse or rat) immunoglobulin. The non-human immunoglobulin providing the CDRs is called the "donor" and the human immunoglobulin providing the framework is called the "acceptor" (humanization by grafting non-human CDRs onto human framework and constant regions, or by incorporating the entire non-human variable domains onto human constant regions (chimerization). Constant regions need not be present, but if they are, they must be substantially identical to human immunoglobulin constant regions, i.e., at least about 85-90%, preferably about 95% or more identical. Hence, all parts of a humanized immunoglobulin, except possibly the CDRs and a few residues in the heavy chain constant region if modulation of the effector functions is needed, are substantially identical to corresponding parts of natural human immunoglobulin sequences. Through humanizing antibodies, biological half-life may be increased, and the potential for adverse immune reactions upon administration to humans is reduced.

The term "fully human" immunoglobulin (or "fully-human" antibody) refers to an immunoglobulin comprising both a human framework region and human CDRs. Constant regions need not be present, but if they are, they must be substantially identical to human immunoglobulin constant regions, i.e., at least about 85-90%, preferably about 95% or more identical. Hence, all parts of a fully human immunoglobulin, except possibly few residues in the heavy chain constant region if modulation of the effector functions or pharmacokinetic properties are needed, are substantially identical to corresponding parts of natural human immunoglobulin sequences. In some instances, amino acid mutations may be introduced within the CDRs, the framework regions or the constant region, in order to improve the binding affinity and/or to reduce the immunogenicity and/or to improve the biochemical/biophysical properties of the antibody.

The term "recombinant antibody" (or "recombinant immunoglobulin") means antibody produced by recombinant techniques. Recombinant host cells for the production of antibodies include recombinant prokaryotic and eukaryotic cells; preferably mammalian host cells, such as Chinese Hamster Ovary (CHO) cells (including CHO-S cells or CHO-k1 cells). The term "recombinant antibody" therefore refers to an antibody produced in recombinant (e.g. mammalian) cells. Because of the relevance of recombinant DNA techniques in the generation of antibodies, one needs not be confined to the sequences of amino acids found in natural antibodies; antibodies can be redesigned to obtain desired characteristics. The possible variations are many and range from the changing of just one or a few amino acids to the complete redesign of, for example, the variable domain or constant region. Changes in the constant region will, in general, be made in order to improve, reduce or alter characteristics, such as complement fixation (e.g. complement dependent cytotoxicity, CDC), interaction with Fc receptors, and other effector functions (e.g. antibody dependent cellular cytotoxicity, ADCC), pharmacokinetic properties (e.g. binding to the neonatal Fc receptor; FcRn). Changes in the variable domain will be made in order to improve the antigen binding characteristics. In addition to antibodies, immunoglobulins may exist in a variety of other forms including, for example, single-chain or Fv, Fab, and (Fab')2, as well as diabodies, linear antibodies, multivalent or multispecific hybrid antibodies.

The term "antibody portion" refers to a fragment of an intact or a full-length chain or antibody, usually the binding or variable region. Said portions, or fragments, should maintain at least one activity of the intact chain/antibody, i.e. they are "functional portions" or "functional fragments". Should they maintain at least one activity, they preferably maintain the target binding property. Examples of antibody portions (or antibody fragments) include, but are not limited to, "single-chain Fv", "single-chain antibodies", "Fv" or "scFv". These terms refer to antibody fragments that comprise the variable domains from both the heavy and light chains, but lack the constant regions, all within a single polypeptide chain. Generally, a single-chain antibody further comprises a polypeptide linker between the VH and VL domains which enables it to form the desired structure that would allow for antigen binding. In specific embodiments, single-chain antibodies can also be bi-specific and/or humanized.

A "Fab fragment" is comprised of one light chain and the variable and CH1 domains of one heavy chain. The heavy chain of a Fab molecule cannot form a disulfide bond with another heavy chain molecule. A "Fab' fragment" that contains one light chain and one heavy chain and contains more of the constant region, between the CH1 and CH2 domains, such that an interchain disulfide bond can be formed between two heavy chains is called a F(ab')2 molecule. A "F(ab')2" contains two light chains and two heavy chains containing a portion of the constant region between the CH1 and CH2 domains, such that an interchain disulfide bond is formed between two heavy chains. Having defined some important terms, it is now possible to focus the attention on particular embodiments of the instant invention.

The term "buffer" is used according to the art. An "equilibration buffer" is a buffer used to prepare the chromatography resin to receive the sample to be purified. A "loading buffer" refers to the buffer used to load the sample on the chromatography column or on a filter. A "wash buffer" is a buffer used to wash the resin. Depending on the mode of the chromatography, the "wash buffer" will allow the removal of the impurities (in bind/elute mode) or the collection of the purified sample (in flowthrough mode). An "elution buffer" refers to the buffer that is used to unbind the sample from the chromatographic material. This is possible thanks to the change of ionic strength between the load/wash buffers and the elution buffer. The purified sample containing the antibody will thus be collected as an eluate.

The term "resin" or "chromatographic material" refer to any solid phase allowing the separation of the molecule to be purified from the impurities. Said resin or chromatographic material may be an affinity, an anionic, a cationic, an hydrophobic, or a mixed mode resin/chromatographic material.

Units, prefixes and symbols are used according to the standards, i.e. International System of Units (SI).

DETAILED DESCRIPTION OF THE INVENTION

A. General

It was found by the inventors that using the sequence "Protein A chromatography" followed by a first "mixed mode chromatography" in flowthrough followed by a second "mixed mode chromatography" also in flowthrough allows among other to reduce, in a sample of antibodies, the amount of high-molecular weight species such as aggregates, and/or low molecular weight species such as antibody fragments, while keeping host cell proteins (HCPs) in acceptable ranges.

Anti-IL-6 receptor antibodies to be purified according to the process of the present invention are usually secreted by recombinant host cells into the culture medium, from which they can be recovered. The sample of antibodies to be purified according to the process of the present invention is preferably obtained (e.g. from the culture medium) at the time of harvest or post-harvest, should the sample be held for a certain amount of time before purification. In one aspect, therefore, the methods of the invention comprise a step of obtaining a sample of anti-IL-6 receptor antibodies to be purified. The sample can be for instance a crude harvest sample, a clarified harvest sample, or a post-harvest sample optionally equilibrated in an aqueous buffered solution.

Therefore, in a first aspect, the present invention provides a method of purifying an anti-IL-6 receptor (anti-IL-6R) antibody from a sample containing the antibody and impurities, wherein the method comprises the following steps: (a) contacting the sample containing the antibody and the impurities with an affinity chromatography material under conditions such that the antibody binds to the resin and at least a portion of the impurities does not bind to the resin; (b) eluting the antibody from the affinity chromatography material, in order to obtain an eluate; (c) loading the eluate of step (b) onto a first mixed mode chromatography material under conditions such that the antibody does not bind to the resin and at least a portion of the remaining impurities binds to the resin; (d) recovering the flowthrough containing the antibody under conditions such that said recovered flowthrough contains a lower level of impurities than the eluate of step (b), (e) loading the recovered flowthrough containing the antibody of step (d) onto a second mixed mode chromatography material under conditions such that the antibody does not bind to the resin and at least a portion of the remaining impurities binds to the resin; and (f) recovering the flowthrough containing the antibody under conditions such that said recovered flowthrough contains a lower level of impurities than the recovered flowthrough of step (d).

In the context of the present invention as a whole, the impurities are preferably selected from the group comprising or consisting of aggregates of the anti-IL-6 receptor antibody or fragments of said antibody or mixtures thereof, one or more of host cell proteins, endotoxins, viruses, nucleic acid molecules, lipids, polysaccharides, and any combinations thereof.

In a second aspect, the present invention provides a method of obtaining an anti-IL-6 receptor antibody in a monomeric form, wherein the method comprises the following steps: (a) contacting the sample containing the antibody in monomeric form, aggregated form and/or fragmented form with an affinity chromatography material under conditions such that the antibody binds to the resin and at least a portion of the aggregated form and fragmented form does not bind to the resin; (b) eluting the antibody in monomeric form from the affinity chromatography material, in order to obtain an eluate; (c) loading the eluate of step (b) onto a first mixed mode chromatography material under conditions such that the antibody in monomeric form does not bind to the resin and at least a portion of the remaining aggregated form and fragmented form bind to the resin; (d) recovering the flowthrough containing the antibody in monomeric form under conditions such that said recovered flowthrough contains a lower level of aggregated form and fragmented form than the eluate of step (b), (e) loading the recovered flowthrough containing the antibody in monomeric form of step (d) onto a second mixed mode chromatography material under conditions such that the antibody in monomeric form does not bind to the resin and at least a portion of the remaining aggregated form and fragmented form bind to the resin; and (f) recovering the flowthrough containing the antibody in monomeric form under conditions such that said recovered flowthrough contains a lower level of aggregated form and fragmented form than the recovered flowthrough of step (d).

The anti-IL-6 receptor antibody to be purified according to the present invention is preferably a monoclonal antibody, which can be a chimeric antibody, a humanized antibody or a fully human antibody. Preferably, the anti-IL-6 receptor antibody is a humanized monoclonal antibody, preferably tocilizumab. The humanized monoclonal antibody (e.g. tocilizumab) has preferably been produced in recombinant mammalian cells, such as Chinese Hamster Ovary (CHO) cell (including CHO-S cell or CHO-k1 cell). The cell lines (also referred to as "recombinant cells" or "host cells") used in the invention are genetically engineered to express the anti-IL-6 receptor antibody of interest. Methods and vectors for genetically engineering cells and/or cell lines to express said anti-IL-6 receptor antibody of interest are well known to those of skill in the art; for example, various techniques are illustrated in Sambrook et al. (1989, and updates; [1]) or Ausubel et al. (1988, and updates; [2]). The recombinant proteins (here anti-IL-6 receptor antibodies) are usually secreted into the culture medium from which they can be recovered. The recovered proteins can then be purified, or partially purified using known processes and products available from commercial vendors. The purified proteins can then be formulated as pharmaceutical compositions. Suitable formulations for pharmaceutical compositions include those described in Remington's Pharmaceutical Sciences (1995 and updated; [3]).

Typically, the methods according to the invention are performed at room temperature (between 15° C. and 25° C.), except for the loading of step (a) which is typically performed between 2 and 8° C. as the sample containing the antibody to be purified (here an anti-IL-6 receptor antibody of interest) is usually stored in cold conditions (between 2 and 8° C.) after harvest as per standard procedure (see for instance Horenstein et al., 2003; [4]).

The impurities to be removed in the context of the invention as a whole are selected from at least one of the group consisting of aggregates of the (monoclonal) antibody or fragments of said (monoclonal) antibody or mixtures thereof, one or more of host cell proteins, endotoxins, viruses, nucleic acid molecules, lipids, polysaccharides, and any combinations thereof. In one aspect, the invention is for removing aggregates and/or fragments of said (monoclonal) antibody.

The recovered sample of step f), comprising the purified antibody, comprises aggregates at a level of at least 90% lower than the level of aggregates in the sample of step (a). Similarly, said recovered sample comprises fragments at a level of at least 40% lower than the level of fragments in the sample of step (a), and HCPs at a level of at least 90% lower or at least 95% lower than the level of HCPs in the sample of step (a) and below the typical acceptable limit of 100 ppm (such as lower than 50 ppm or 30 ppm).

B. Affinity chromatography step (steps (a) and (b))

B.1. General

The term "Protein A chromatography" refers to the affinity chromatography technique using protein A, in which the protein A is usually immobilized on a solid phase. Protein A is a surface protein originally found in the cell wall of the bacteria *Staphylococcus aureus*. There now exist various kinds of protein A of natural origin or produced recombinantly, possibly comprising some mutations as well. This protein has the ability to specifically bind the Fc portion of immunoglobulin such as IgG antibodies.

Protein A chromatography is one of the most common affinity chromatography techniques used for purifying antibodies. Typically, the antibodies from a solution to be purified reversibly bind to the protein A, via their Fc portion. To the contrary (most of) the impurities flow through the column and are eliminated via washing steps. The antibodies thus need to be eluted from the column, or the affinity resin, in order to be collected for the next purification steps.

The protein A chromatography material in step a) in the context of the present invention as a whole is selected for instance from the group, but not limited to, consisting of MABSELECT™, MABSELECT™ SuRe, MABSELECT™ SuRe LX, AMSPHERE™ A3, TOYOPEARL® AF-rProtein A-650F, TOYOPEARL® AF-HC, PROSEP®-vA, PROSEP®-vA Ultra, PROSEP® Ultra Plus or ESHMUNO-A®. In some embodiments, the Protein A ligand is immobilized on a matrix selected from the group consisting of dextran based matrix, agarose based matrix, polystyrene based matrix, hydrophilic polyvinyl ethyl based matrix, rigid polymethacrylate based matrix, porous polymer based matrix, controlled pore glass based matrix and any combination thereof. Alternatively, the Protein A ligand is immobilized on a membrane.

The purpose of this step is to capture the antibodies (e.g. monoclonal antibodies such as toclizumab) present in the sample (e.g. a clarified harvest sample), concentrate them, and remove most of process-related impurities (such as HCPs, DNA, components of the cell culture broth).

B.2. Equilibration and Loading

In the context of the present invention as a whole, the sample, containing the anti-IL-6 receptor antibody of interest (e.g. tocilizumab), to be contacted with the affinity chromatography material in step a) is in an aqueous solution. It can be a crude harvest, a clarified harvest, or even a sample pre-equilibrated in an aqueous buffered solution. Before purification of the sample, the Protein A material has to be equilibrated. This equilibration is performed with an aqueous buffered solution.

Suitable aqueous buffered solution (or buffers) include, but are not limited to, phosphate buffers, Tris (tris(hydroxymethyl)aminomethane) buffers, acetate buffers, and/or citrate buffers. The aqueous buffered solution for this step is preferably based on sodium acetate or sodium phosphate. Preferably, the buffered solution is at a concentration in the range of or of about 10 mM to or to about 40 mM and a pH in the range of or of about 6.5 to or to about 8.0. Even preferably, the buffered solution is at a concentration in the range of or of about 15 mM to or to about 30 mM (such as between 20 and 30 mM) and its pH in the range of or of about 6.8 to or to about 7.5 (such as between 6.5 and 7.5). Even preferably, the concentration of the buffered solution is at or at about 15.0, 16.0, 17.0, 17.0, 18.0, 19.0, 20.0, 21.0, 22.0, 23.0, 24.0 or 25.0 mM and its pH is at or at about 6.8, 6.9, 7.0, 7.1, 7.2, 7.3, 7.4 and 7.5.

The aqueous buffered solution to be used in one of the methods according to the invention can further comprise a salt at a concentration in the range of or of about 100 mM to or to about 200 mM, preferably at a concentration in the range of or of about 125 to 180 mM, such as of or of about 130, 135, 140, 145, 150, 155, 160, 165, or 170 mM. Preferably the salt is sodium chloride. In one aspect, the aqueous buffered solution comprises sodium phosphate at a concentration between 20 and 30 mM, a salt (e.g. sodium chloride) at a concentration between 100 and 200 mM, and/or has a pH in the range of 6.5 to about 7.5. For instance, the aqueous buffered solution can comprise sodium phosphate at a concentration of or of about 25 mM, sodium chloride at a concentration of or of about 150 mM, and has a pH of or of about pH 7.0±0.2.

The skilled person will choose the appropriate conditions for equilibration and loading in order that the anti-IL-6 receptor antibody to be purified, such as tocilizumab, does bind to the affinity chromatography (e.g. Protein A chromatography) material. To the contrary, at least a part of the impurities will flow through the chromatography material (i.e. will not bind to the resin). For instance, the sample (e.g. clarified harvest sample) containing antibodies to be purified may be loaded at an amount of or of about 35-40 g antibody per litre of packed affinity chromatography material, such as at an amount of or of about 37-40 g antibody per litre of packed affinity chromatography material, such as at an amount of or of about 37 g or 40 g antibody per litre of packed affinity chromatography material.

B.3. Washing

After loading (step (a)), the affinity chromatography material is washed once or twice, with more of the same solution as the equilibration buffer or a different one, or a combination of both. As for the equilibration and loading step, suitable aqueous buffered solution (or buffers) include, but are not limited to, phosphate buffers, Tris (tris(hydroxymethyl)aminomethane) buffers, acetate buffers, and/or citrate buffers. The wash step is necessary to remove the unbound impurities.

Preferably, the wash is performed in one step, i.e. with one buffer. Preferably the wash buffer is an acetate buffer (such as a sodium acetate buffer) at a concentration in the range of or of about 40 mM to or to about 70 mM and a pH in the range of or of about 5.0 to or to about 6.0. Even preferably, the buffered solution is at a concentration in the range of or of about 45 mM to or to about 65 mM and its pH in the range of or of about 5.2 to or to about 5.8. Even preferably, the concentration of the buffered solution is at or at about 50, 51, 52, 53, 54, 55, 56, 57, 58, 59 or 60 mM and its pH is at or at about 5.2, 5.3, 5.4, 5.5, 5.6, 5.7 and 5.8.

In an alternative, the wash is performed in two steps with two different buffers. Preferably the first wash buffer is an acetate buffer (such as a sodium acetate buffer) at a concentration in the range of or of about 40 mM to or to about 70 mM and a pH in the range of or of about 5.0 to or to about 6.0. Even preferably, the buffered solution is at a concentration in the range of or of about 45 mM to or to about 65 mM and its pH in the range of or of about 5.2 to or to about 5.8. Even preferably, the concentration of the buffered solution is at or at about 50, 51, 52, 53, 54, 55, 56, 57, 58, 59 or 60 mM and its pH is at or at about 5.2, 5.3, 5.4, 5.5, 5.6, 5.7 and 5.8. Preferably, the second wash buffer is similar to the equilibration/loading buffer. For example, the second wash buffer is a phosphate (e.g. sodium phosphate) buffer at a concentration in the range of or of about 15 mM to or to about 30 mM (such as between 20 and 30 mM) and having a pH in the range of or of about 6.8 to or to about 7.5 (such as between 6.5 and 7.5). The aqueous buffered solution to be used in one of the methods according to the invention can further comprise a salt. Preferably, should a salt be present and should the method comprise a two-wash-step, said salt will be in a higher concentration in the first wash buffer than in the second wash buffer. Preferably, the concentration of salt in the wash buffer (when 1-step only) or in the first wash buffer (when 2-steps), if any, is at a concentration in the range of or of about 1.0 M to or to about 2.0 M, preferably at a concentration in the range of or of about 1.25 to 1.80 M, such as of or of about 1.3, 1.35, 1.4, 1.45, 1.5, 1.55, 1.6, 1.65, or 1.70 M. Preferably, the concentration of salt in the second wash buffer, if any, is at a concentration in the range of or of about 100 mM to or to about 200 mM, preferably at a concentration in the range of or of about 125 to 180 mM, such as of or of about 130, 135, 140, 145, 150, 155, 160, 165, or 170 mM. Suitable salts include, but are not limited to, sodium chloride, potassium chloride, ammonium chloride, sodium acetate, potassium acetate, ammonium acetate, calcium salts, and/or magnesium salts. In one aspect, the salt is sodium chloride.

The skilled person will chose the appropriate conditions for washing step in order that the anti-IL-6 receptor antibody to be purified, such as tocilizumab, remains bound to the affinity chromatography material. To the contrary, at least a part of the impurities will continue to flow through the chromatography material thanks to the wash buffers. As a non-limiting example, with a 2-steps wash, if the equilibration buffer comprises sodium phosphate at a concentration of or of about 25 mM, a salt (e.g. NaCl) at a concentration of or of about 150 mM and has a pH at or at about 7.0±0.2, a first wash can be performed with a wash buffer comprising acetate (e.g. sodium acetate) (or phosphate) at a concentration of or of about 55 mM, a salt (e.g. NaCl) at a concentration of or of about 1.5 M and a pH of or of about 5.5±0.2, and a second wash can be performed with a wash buffer identical to the equilibration buffer.

B.4. Elution

The anti-IL-6 receptor antibody, such as tocilizumab, can then be eluted (step (b)) using a solution (called elution buffer) that interferes with the binding of the affinity chromatography material to the constant domain of the antibody to be purified (here the anti-IL-6 receptor antibody). This elution buffer may include acetic acid, acetate glycine, citrate or citric acid. Preferably, the buffered solution is an acetic acid buffer at a concentration in the range of or of about 40 mM to or to about 70 mM. More preferably, the buffered solution is at a concentration in the range of or of about 45 mM to or to about 65 mM. Even more preferably, the concentration of the buffered solution is at or at about 50, 51, 52, 53, 54, 55, 56, 57, 58, 59 or 60 mM; such as acetic acid buffer at 55 mM. Elution may be performed by lowering the pH of the chromatography material and the antibody attached thereto. For example, the pH of the elution buffer can be at or at about 4.5 or less, or at or at about 4.0 or less. It is preferably at or at about 2.8 to or to about 3.7, such as 2.9, 3.0, 3.1, 3.2, 3.3, 3.4, 3.5 or 3.6; such as at pH 3.2±0.2. The elution buffer optionally includes a chaotropic agent.

The skilled person will chose the appropriate conditions for elution step in order that the anti-IL-6 receptor antibody to be purified, such as tocilizumab, is released from the affinity chromatography material. As a non-limiting example, the elution (i.e. elution of step (b)) can be performed with an elution buffer comprising acetic acid at a concentration of or of about 55 mM and a pH of 3.2±0.2.

C. Mixed mode chromatography steps

C.1. General

The mixed mode support according to the present invention refers to a chromatographic solid phase that involves a combination of two or more of the following functionalities (but not limited to): cation exchange, anion exchange, hydrophobic interaction, hydrophilic interaction, hydrogen bonding, pi-pi bonding, or metal affinity. It thus comprises two different types of ligands. The solid phase can be a porous particle, nonporous particle, membrane, or monolith.

C.2. First mixed mode chromatography (steps (c) and (d))

In the context of the present invention as a whole, the mixed mode chromatography material for step (c) involves a combination of two or more of cation exchange, anion exchange, hydrophobic interaction, hydrophilic interaction, and hydrogen bonding; preferably involving at least anion exchange. The preferred mixed mode support for step (c) is selected from the group consisting of CAPTO™ MMC, CAPTO™ adhere, CAPTO™ adhere ImpRes, MEP (mercaptoethylpyridine) HYPERCEL™ and ESHMUNO™ HCX. It is preferably CAPTO™ adhere, having anion exchange properties.

Preferably, the eluate recovered after affinity chromatography (i.e. eluate of step (b)) is adjusted to a pH of 7.5 to 8.5, such as 7.5, 7.6, 7.7, 7.8, 7.9, 8.0, 8.1, 8.2, 8.3, 8.4 or 8.5. The conductivity of the eluate may also be adjusted, such as to or to about 10-20 mS/cm, such as to 15±0.5 mS/cm. Adjustment can be done with a concentrated solution of Tris (tris(hydroxymethyl)aminomethane) and/or NaOH for instance; such as using 2M Tris (tris(hydroxymethyl)aminomethane) buffer. The aim is to have the eluate of step (b) at a pH and conductivity similar to the one under which step (c) is to be performed. If step (c) for instance is to be performed at a pH of 8.0±0.2, the eluate of step (b) has to be adjusted to a pH of 8.0±0.2. Similarly if step (c) is to be performed with a salt (e.g. NaCl), same salt conditions will be used for the adjustment. As discussed below, the eluate (e.g. after adjustment) may optionally be depth filtered prior to loading onto the first mixed mode chromatography material.

Before being loaded with the eluate (e.g. adjusted and/or depth-filtered eluate), the first mixed mode chromatography material is equilibrated with an aqueous buffered solution (equilibration buffer). Suitable aqueous buffered solution (or buffers) include, but are not limited to, phosphate buffers, Tris (tris(hydroxymethyl)aminomethane) buffers, acetate buffers, and/or citrate buffers. Preferably, the buffered solution is a phosphate (e.g. sodium phosphate) buffer. The buffered solution (e.g. a sodium phosphate buffer) is preferably at a concentration in the range of or of about 20 mM to or to about 60 mM and a pH in the range of or of about 7.5 to or to about 8.5. Even preferably, the buffered solution is at a concentration in the range of or of about 30 mM to or to about 50 mM and its pH in the range of or of about 7.5 to or to about 8.5. Even preferably, the concentration of the buffered solution is at or at about 35.0, 36.0, 37.0, 38.0, 39.0, 40.0, 41.0, 42.0, 43.0, 44.0 or 45.0 mM and its pH is at or at about 7.7, 7.8, 7.9, 8.0, 8.1, 8.2 or 8.3.

The aqueous buffered solution to be used in one of the methods according to the invention can further comprise a salt at a concentration in the range of or of about 75 mM to or to about 125 mM, preferably at a concentration in the range of or of about 85 to 120 mM or 85 to 110 mM, such as of or of about 90, 91, 92, 93, 94, 95, 96, 97, 98, 99 or 100 mM. Suitable salts include, but are not limited to, sodium chloride and/or potassium chloride; preferably sodium chloride. In one aspect, the first mixed mode chromatography material is equilibrated with an equilibration buffer that is an aqueous buffered solution comprising sodium phosphate at a concentration between 30 and 50 mM, a salt (e.g. NaCl) at a concentration between 80 and 120 mM, and a pH in the range of 7.5 to 8.5.

The equilibration buffer will also be used to "push" the unbound antibodies/proteins (anti-IL-6 receptor antibody) in the flowthrough, in order to recover said purified antibodies/proteins (step d).

In the context of the invention, the skilled person will chose the appropriate conditions for this first mixed mode chromatography step in order that the anti-IL-6 receptor antibody to be purified, such as tocilizumab, does not bind to the first mixed mode chromatography material, i.e. in order that it flows through the chromatography material. Said flowthrough is recovered at the bottom of the column. To the contrary, at least a part of the impurities bind to the chromatography material. As a non-limiting example, the equilibration buffer for the first mixed mode chromatography step comprises sodium phosphate at a concentration of or of about 40 mM, a sodium chloride at a concentration of or of about 95 mM and a pH of 8.0±0.2. Loading is performed in the same condition. For instance, the first mixed mode chromatography material can be loaded with eluate at an amount of or of about 80 to or to about 120 g anti-IL-6 receptor antibody(e.g. toclizumab) per litre of packed resin; such as at an amount of or of about 110 g antibody per litre of packed resin.

C.3. Second mixed mode chromatography (steps (e) and (f))

In the context of the present invention as a whole, the preferred mixed mode support for the second mixed mode chromatography step (step (e)) is selected from the group consisting of hydroxyapatite-based ligand (or resin), hydroxyfluorapatite-based ligand (or resin) or fluorapatite-based ligand (or resin).

An hydroxyapatite-based resin is a mixed mode support comprising a mineral of calcium phosphate with the structural formula $Ca_5(PO_4)_3OH)_2$. Its dominant modes of interaction are phosphoryl cation exchange and calcium metal affinity. Hydroxyapatite-based resins are commercially available in various forms, including but not limited to ceramic composite forms. Commercial examples of ceramic hydroxyapatite include, but are not limited to CHT™ Type I and CHT™ Type II. Ceramic hydroxyapatites are porous particles and can have various diameters, for instance about 20, 40, and 80 microns.

A fluorapatite-based resin is a mixed mode support comprising an insoluble fluoridated mineral of calcium phosphate with the structural formula $Ca_5(PO_4)_3F$ or $Ca_{10}(PO_4)_6F_2$. Its dominant modes of interaction are phosphoryl cation exchange and calcium metal affinity. Fluorapatite-based resins are commercially available in various forms, including but not limited to ceramic composite forms. Commercial examples of ceramic fluorapatite include, but are not limited to CFT™ Type I and CFT™ Type II. Ceramic fluorapatites are spherical porous particles and can have various diameters, for instance about 10, 20, 40, and 80 microns.

A hydroxyfluorapatite-based resin a mixed mode support comprising an insoluble hydroxylated and an insoluble fluoridated mineral of calcium phosphate with the structural formula $Ca10(PO4)6(OH)x(F)y$. Its dominant modes of interaction are phosphoryl cation exchange and calcium metal affinity. Hydroxyfluorapatite is commercially available in various forms, including but not limited to ceramic, crystalline and composite forms. Composite forms contain hydroxyfluorapatite microcrystals entrapped within the pores of agarose or other beads. An example of ceramic hydroxyfluorapatite resin is the MPC Ceramic Hydroxyfluorapatite Resin™, with a structural formula $(Ca_{10}(PO_4)_6 (OH)_{1.5}(F)_{0.5})$, It is based on the ceramic apatite Type I (40 µm) mixed-mode resin.

Preferably, the flowthrough recovered after the first mixed mode chromatography (i.e. eluate of step (d)) is adjusted to a pH of 7.0 to 8.5 such as 7.2, 7.3, 7.4, 7.5, 7.6, 7.7, 7.8, 7.9 or 8.0. Adjustment can be done with a concentrated solution of Tris (tris(hydroxymethyl)aminomethane) and/or NaOH for instance. The aim is to have the flowthrough of step (d) into conditions suitable for the load on the second mixed mode chromatography. If step (e) for instance is to be performed at a pH of 7.5±0.2, the flowthrough of step (d) has to be adjusted to a pH of 7.5±0.2. This step of adjustment can be performed together with a concentration step, such as via tangential flow filtration (TFF). In such a case, a filtration step can be added before the second mixed mode chromatography. Other adjustments that are needed relate to salts (e.g. NaCl) and $NaPO_4$.

Before being loaded with the optionally-adjusted and/or concentrated flowthrough, the second mixed mode chromatography material is equilibrated with an aqueous buffered solution (equilibration buffer). Preferably, the flowthrough recovered after the first mixed mode chromatography step (step (d)) is equilibrated prior to loading onto the second mixed mode chromatography material (of step (e)) with an aqueous buffered solution. Suitable aqueous buffered solution (or buffers) include, but are not limited to, phosphate buffers, Tris (tris(hydroxymethyl)aminomethane) buffers, acetate buffers, and/or citrate buffers. Preferably, the buffered solution is a phosphate (e.g. sodium phosphate) buffer. The buffered solution (e.g. a sodium phosphate buffer) is preferably at a concentration in the range of or of about 1 mM to or to about 20 mM and a pH in the range of or of about 7.0 to or to about 8.0. More preferably, the buffered solution is at a concentration in the range of or of about 2 mM to or to about 15 mM and its pH in the range of or of about 7.2 to or to about 7.8. Even more preferably, the concentration of the buffered solution is at or at about 3.0, 3.5, 4.0, 4.5, 5.0, 5.5, 6.0, 6.5, 7.0, 8.0, 9.0, 10.0 mM and its pH is at or at about 7.2, 7.3, 7.4, 7.5, 7.6, 7.7 and 7.8.

The aqueous buffered solution to be used in one of the methods according to the invention can further comprises a salt at a concentration in the range of or of about 100 mM to or to about 250 mM, preferably at a concentration in the range of or of about 130 to 200 mM, such as of or of about 140, 145, 150, 155, 160, 165, 170, 175, 180, 185, 190 or 195 mM. Suitable salts include, but are not limited to, sodium chloride and/or potassium chloride; preferably sodium chloride. In one aspect, the second mixed mode chromatography material is equilibrated with an equilibration buffer that is an aqueous buffered solution comprising sodium phosphate at a concentration between 1 and 10 mM, optionally a salt (e.g. NaCl) at a concentration between 130 and 200 mM, and a pH in the range of 7.0 to 8.0.

The equilibration buffer will also be used to "push" the unbound antibodies/proteins in the flowthrough, in order to recover said purified antibodies/proteins (step f).

In the context of the invention, the skilled person will chose the appropriate conditions for this second mixed mode chromatography step in order that the anti-IL-6 receptor antibody to be purified, such as tocilizumab, does not bind to the first mixed mode chromatography material, i.e. in order that it flows through the chromatography material.

Said flowthrough is recovered at the bottom of the column. To the contrary, at least a part of the impurities bind to the chromatography material. As a non-limiting example, the second mixed mode chromatography step can be performed in an aqueous buffered solution comprising 5 mM sodium phosphate, 170 mM sodium chloride and a pH of 7.5±0.2. Loading is performed in the same condition. For instance, the second mixed mode chromatography material can be loaded with eluate at an amount of at least 60 g anti-IL-6 receptor antibody (e.g. toclizumab) per litre of packed resin; such as at an amount of or of about 60 g antibody per litre of packed resin. In one embodiment, the second mixed mode chromatography material can be loaded with eluate at an amount of or of about 80 to or to about 120 g anti-IL-6 receptor antibody (e.g. toclizumab) per litre of packed resin; such as at an amount of or of about 110 g antibody per litre of packed resin.

D. Possible additional steps

D.1. Virus inactivation

Optionally, the method according to the present invention comprises a step of virus inactivation. This step is preferably performed between the affinity chromatography step (after elution of the antibody) and the first mixed mode chromatography step. It is called step (b'). In order to inactivate virus, the eluate recovered after affinity chromatography step (i.e. the eluate of step (b)) is adjusted with a concentrated acidic aqueous solution. The pH to be reached during adjustment is preferably in a range of or of about 3.0 to or to about 4.5, even preferably in a range of or of about 3.2 to or to about 4.0, such as 3.2, 3.3, 3.4, 3.5, 3.6, 3.7, 3.8, 3.9 or 4.0; typically pH 3.5±0.2. The concentration of the salt in the acidic aqueous solution used for adjustment is at or at about 1.5 to or to about 2.5. Preferably, the concentration of the salt in the acidic aqueous solution is at or at about 1.7 to or to about 2.3, such as 1.7, 1.8, 1.9, 2.0, 2.1, 2.2, or 2.3 M. The preferred acidic aqueous solution is acetic acid; such as at a concentration of or of about 2M. In one aspect, the eluate is adjusted to pH 3.5±0.2 using 2M acetic acid. The resulting adjusted eluate is typically incubated for about 60±15 min.

At the end of the incubation, the material is then neutralized with a concentrated neutral aqueous solution. The pH to be reached during neutralization is preferably in a range of or of about 4.5 to or to about 6.5, should the neutralized sample be held before step (c), even preferably in a range of or of about 4.8 to 5.6 such as 4.8, 4.9, 5.0, 5.1, 5.2, 5.3, 5.4, 5.5 or 5.6. Should the neutralized sample be directly used for step (c), pH to be reached during neutralization will be the same pH as the one that will be used for step (c), i.e. from 6.5 to 8.5 (such as from 7.5 to 8.5, such as pH 8±0.2). The concentration of the salt in the aqueous solution used for neutralization is at or at about 1.0 to or to about 2.5. Preferably, the concentration of the salt in the neutral aqueous solution is at or at about 1.0 to or to about 2.0, such as 1.0, 1.1, 1.2, 1.3, 1.4, 1.5, 1.6, 1.7, 1.8, 1.9, 2.0 M. The preferred neutral aqueous solution is Tris (tris(hydroxymethyl)aminomethane) base; such as at 2M. In one aspect, the virus-inactivated material is neutralized to pH 5.2±0.2 using 2M Tris (tris(hydroxymethyl)aminomethane) base.

D.2. Optional Filtration Steps

Various filtration steps can be added in the purification process. Such steps may be needed to further eliminate impurities but can also be used to concentrate the sample to be purified before the next chromatographic step or to change the buffer before the next chromatographic step.

For instance, in order to further reduce impurities of the eluate, or adjusted eluate, after step (b) or (b'), a filtration step can be performed just before the first mixed mode chromatography. This filtration step is preferably performed with a depth filter. Said step can be performed in line with the first mixed mode chromatography.

A filtration step, such as a depth filtration, can be included during the process. This step can for instance be added just before the first mixed mode chromatography, as described in Example 2.

Tangential Flow Filtration (TFF) can also be performed during the purification procedure. For instance, should one wish to concentrate the flowthrough from step (d) before being loading on the second mixed mode chromatography, a TFF can be performed just before step (e). Such step, if any, is called step (d'). Such filtration step can be performed with the equilibration buffer that will be used for the second mixed mode chromatography. This will allow the flowthrough not only to be concentrated but also to be in such a condition to be ready for the next chromatographic step. As a non-limiting example, should the second mixed mode chromatography step be performed in an aqueous buffered solution comprising 5 mM sodium phosphate, 170 mM sodium chloride, pH 7.5±0.2, the TFF step can be performed in an aqueous buffered solution comprising 5 mM sodium phosphate, 170 mM sodium chloride, pH 7.5±0.2.

DESCRIPTION OF THE SEQUENCE

SEQ ID NO 1: light chain of tocilizumab, amino acid sequence

SEQ ID NO 2: heavy chain of tocilizumab, amino acid sequence

EXAMPLES

I. Cells, Cell Expansion and Cell Growth

The anti-IL-6R antibody used in the example is tocilizumab (see SEQ ID Nos. 1-2). It was produced in CHO-K1 cells. Cells were cultured in fed-batch culture. They were incubated at 36.5° C., 5% de $CO_2$, 90% humidity and shaken at 320 rpm. Each of the fed-batch culture lasted 14 days.

II. Analytical Methods

Content in HCPs (ppm): HCPs level in ppm is calculated using the HCPs level determined in ng/mL divided by the mAb concentration determined by UV absorbance (mg/mL).

Content in aggregates (HMW) (expressed in %): the assessment was done by SE-HPLC, using a standard protocol.

Content in Low Molecular weight (LMW) (expressed in %): the assessment was done by CE-SDS, using a standard protocol.

Example 1—Tocilizumab Purified According to a Standard Process

The full purification process was performed at room temperature (15-25° C.) except for the load step of the Protein A step, as the clarified harvest was stored at 2-8° C. before purification.

Tocilizumab was purified according to standard purification steps including "protein A chromatography" followed by a first "ion exchange chromatography" in bind elute followed by a second "ion exchange chromatography" in flowthrough (also called polishing step).

Using said standard process, the following results were obtained:

| Impurities | Post Protein A | Post first IEX | Post Second IEX | Total purification Factor |
|---|---|---|---|---|
| HCPs | 250 ppm | 50 ppm | 5 ppm | 50 |
| HMW | 1% | 0.6% | 0.6% | 1.7 |
| LMW | 2.8% | 3.1% | 3% | 0.9 |

Example 2—Tocilizumab Purified According to the Process of the Invention

The full purification process was performed at room temperature (15-25° C.) except for the load step of the Protein A step, as the clarified harvest was stored at cold temperature before purification (i.e. at 2-8° C.). The new process, according to the invention, had been used to improve the purification scheme for tocilizumab. The main steps for this new process were:

Protein A chromatography,
Mixed mode chromatography 1,
Mixed mode chromatography 2.

Protein a Step (PUP)

Protein a step was performed on a Prosep Ultra Plus® resin (from Merck Millipore), with a target bed height of 20±2 cm. This step was performed under the following conditions:

1. Equilibration: at least (≥) 5 bed volume (BV) of an aqueous solution comprising 25 mM NaPI (sodium phosphate)+150 mM NaCl, pH 7.0. At the end of equilibration, the pH and conductivity of the effluent were checked. They should meet the recommendations of pH and conductivity of 7.0±0.2 and 18±1 mS/cm, respectively, before loading can start.
2. Load: clarified harvest at a maximum capacity of about 35-40 g tocilizumab/L of packed bed, at a temperature of 2-25° C.
3. Wash I: ≥5 BV of a solution comprising 55 mM sodium Acetate, 1.5M NaCl, pH 5.5.
4. Wash II: ≥3 BV of a solution comprising 25 mM NaPI+150 mM NaCl, pH 7.0.
5. Elution: the column was eluted with 55 mM acetic acid pH3.2. The eluate peak was collected as soon as the absorbance at 280 nm reaches 25 mAU/mm of UV cell path and the collection was stopped as soon as the absorbance at 280 nm is back at 25 mAU/mm of UV cell path. The eluate volume should be less than 4BV.

Virus Inactivation at Low pH

The Protein A eluate was adjusted to pH 3.5±0.2 by addition of 2M acetic acid solution under stirring. Once the target pH was reached, the agitation was stopped and the acidified eluate was incubated for 60±15 min. At the end of the incubation, the material was neutralized to pH 5.2±0.2 by addition of 2M Tris (tris(hydroxymethyl)aminomethane) base solution under stirring. The resulting eluate (neutralized eluate) can be stored at least 3 months at 2-8° C.

Mixed mode chromatography 1 (MM1)

The neutralized eluate was adjusted to pH 8.0±0.2 with 2M Tris (tris(hydroxymethyl)aminomethane) and its conductivity was increased to 15.0±0.5 mS/cm with 3M NaCl. This adjusted eluate was then submitted to depth filtration in-line with mixed mode chromatography on CAPTO™ adhere (from GE Healthcare) as follows:

1. The depth filter (Millistack Pod from Merck Millipore) was connected to the purification system in front of the chromatography column.
2. Pre equilibration of the resin: 3BV of 500 mM NaPI, pH 7.5
3. Equilibration of the resin: 6BV of 40 mM NaPI, 93 mM NaCl, pH 8.0.
4. Load the adjusted eluate at a capacity of 80-120 g/L of tocilizumab/L of packed resin (set point: 110 g tocilizumab/L of packed resin). Start collection of the flow through as soon as the absorbance at 280 nm reaches 12.5 mAU/mm of UV cell path.
5. Wash: 4BV of 40 mM NaPI, 93 mM NaCl, pH 8.0. Stop collection of the flowthrough containing the purified tocilizumab.

Mixed Mode Chromatography 2 (MM2)

Before being further purified in the mixed mode chromatography 2, the flowthrough from mixed mode chromatography 1 was concentrated via TFF, on a Pellicon 3 Ultracel® 30 kDa membrane (from Merck Millipore). This step allowed also to exchange the buffer into conditions suitable for the load of the Fluorapatite chromatography step, on a CFT Ceramic Fluorapatite® Type II (40 um) (from Bio-Rad).

The TFF step was performed as follows:

1. Equilibration of the filter (comprising both retentate and permeate lines) with a buffer containing 5 mM NaPO4, 170 mM NaCl, pH 7.5 buffer.
2. Load the flowthrough from mixed mode chromatography 1 at 500 g tocilizumab/m²
3. Diafilter with ≥9DV of the same buffer as for equilibrium
4. Recover the retentate containing the purified tocilizumab.

The mixed mode chromatography 2 step was performed as follows:

1. Pre equilibration: ≥3BV of 0.5M NaPI, pH 7.50.
2. Equilibration: ≥5BV 5 mM NaPI, 170 mM NaCl, pH7.5
3. Load the TFF retentate at a capacity ≤60 g tocilizumab/L of packed resin. Start collection of the flow through as soon as the absorbance at 280 nm reaches 12.5 mAU/mm of UV cell path.
4. Wash: ≥6BV with 5 mM NaPI, 170 mM NaCl, pH7.5. Stop collection of the flowthrough containing the purified tocilizumab.

Using said new process, the following results were obtained:

| Impurities | Post PUP | Post MM1 | Post MM2 | Total purification Factor |
|---|---|---|---|---|
| HCPs | 874 ppm | 36.7 ppm | 25.1 ppm | 35 |
| HMW | 2.4% | 0.5% | 0.2% | 12 |
| LMW | 2.7% | 2.3% | 1.4% | 1.9 |

CONCLUSION

It was found by the inventors that using the new process according to example 2, the purification of an anti-IL-6 receptor antibody (such as tocilizumab) was improved compared to a standard process (as described in example 1). In particular it was possible to decrease even more the quantity of impurities such as aggregates (HMW content) and fragments (LMW content), while keeping HCPs in acceptable ranges.

REFERENCES

[1] Sambrook et al., 1989 and updates, Molecular Cloning: A Laboratory Manual, Cold Spring Laboratory Press.

[2] Ausubel et al., 1988 and updates, Current Protocols in Molecular Biology, eds. Wiley & Sons, New York.

[3] Remington's Pharmaceutical Sciences, 1995, 18th ed., Mack Publishing Company, Easton, PA.

[4] Horensetein et al., 2003, Journal of Immunological Methods 275:99-112.

---

The invention claimed is:

1. A method of purifying a mono-specific anti-IL-6 receptor antibody from a sample containing said antibody and impurities, wherein the anti-IL-6 receptor antibody is tocilizumab, the impurities comprise host cell proteins, aggregates of the anti-IL-6 receptor antibody and fragments of the anti-IL-6 receptor antibody, and the method comprises the following steps:
   (a) contacting the sample containing the antibody and the impurities with a protein A chromatography material under conditions such that the antibody binds to the protein A chromatography material and at least a portion of the impurities does not bind to the protein A chromatography material;
   (b) eluting the antibody from the Protein A chromatography material, in order to obtain an eluate;
   (c) loading the eluate of step (b) onto a first mixed mode chromatography material under conditions such that the antibody does not bind to the first mixed mode chromatography material and at least a portion of the remaining impurities binds to the first mixed mode chromatography material, wherein the first mixed mode chromatography material is a N-benzyl-N-methyl ethanol amine ligand;
   (d) recovering the flowthrough containing the antibody under conditions such that said recovered flowthrough contains a lower level of impurities than the eluate of step (b),
   (e) loading the recovered flowthrough containing the antibody of step (d) onto a second mixed mode chromatography material under conditions such that the antibody does not bind to the second mixed mode chromatography material and at least a portion of the remaining impurities binds to the second mixed mode chromatography material; wherein the second mixed mode chromatography material is a fluorapatite-based ligand of ceramic fluoroapatite type I or ceramic fluoroapatite type II; and
   (f) recovering the flowthrough containing the antibody under conditions such that said recovered flowthrough contains a lower level of impurities than the recovered flowthrough of step (d).

2. The method according to claim 1, wherein the antibody has been produced in recombinant mammalian cells.

3. The method according to claim 1, wherein the sample, containing the anti-IL-6 receptor antibody, to be contacting with the Protein A chromatography material in step a) is in an aqueous solution.

4. The method according to claim 1, wherein the protein A chromatography material is equilibrated, before step (a), with an aqueous buffered solution comprising sodium phosphate at a concentration between 20 and 30 mM, and a salt at a concentration between 100 and 200 mM and a pH in the range of 6.5 to about 7.5.

5. The method according to claim 1, wherein the elution of step (b) is performed with an elution buffer comprising acetic acid at a concentration between 40 and 70 mM and at a pH in the range of 3.0 to about 3.5.

6. The method according to claim 1, wherein prior to loading the eluate of step (b) onto the first mixed mode chromatography material of step (c), the first mixed mode chromatography material is equilibrated with an aqueous buffered solution comprising sodium phosphate at a concentration between 30 and 50 mM, a salt at a concentration between 80 and 120 mM, and a pH in the range of 7.5 to about 8.5.

7. The method according to claim 1, wherein prior to loading the recovered flowthrough of step (d) onto the second mixed mode chromatography material of step (e), the second mixed mode chromatography material is equilibrated with an aqueous buffered solution comprising sodium phosphate at a concentration between 1 and 10 mM, optionally a salt at a concentration between 130 and 200 mM and a pH in the range of 7.0 to about 8.0.

8. The method according to claim 4, wherein the salt is sodium chloride.

* * * * *

SEQUENCE LISTING

```
<160> NUMBER OF SEQ ID NOS: 2

<210> SEQ ID NO 1
<211> LENGTH: 107
<212> TYPE: PRT
<213> ORGANISM: Artificial sequence
<220> FEATURE:
<223> OTHER INFORMATION: Light chain tocilizumab

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys
            100                 105

<210> SEQ ID NO 2
<211> LENGTH: 119
<212> TYPE: PRT
<213> ORGANISM: Artificial sequence
<220> FEATURE:
<223> OTHER INFORMATION: Heavy chain tocilizumab
<220> FEATURE:
<221> NAME/KEY: misc_feature
<222> LOCATION: (1)..(1)
<223> OTHER INFORMATION: Xaa can be any naturally occurring amino acid

<400> SEQUENCE: 2

Xaa Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80
```

```
Leu Arg Leu Ser Ser Val Thr Ala Ala Asp Thr Ala Val Tyr Tyr Cys
            85              90                  95

Ala Arg Ser Leu Ala Arg Thr Thr Ala Met Asp Tyr Trp Gly Gln Gly
            100             105                 110

Ser Leu Val Thr Val Ser Ser
        115
```